US00PP21170P3

(12) United States Plant Patent
Chin et al.

(10) Patent No.: US PP21,170 P3
(45) Date of Patent: Jul. 20, 2010

(54) **MALE *ASPARAGUS* HYBRID PLANT 'NJ953'**

(50) Latin Name: *Asparagus officinalis*
Varietal Denomination: NJ953

(75) Inventors: Chee-kok Chin, Holmdel, NJ (US); Stephen A. Garrison, Pittsgrove, NJ (US); John J. Kinelski, Princeton, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 12/074,609

(22) Filed: Mar. 4, 2008

(65) Prior Publication Data

US 2009/0229027 P1 Sep. 10, 2009

(51) Int. Cl.
*A01H 5/00* (2006.01)

(52) U.S. Cl. ..... Plt./260

(58) Field of Classification Search ..... Plt./260
See application file for complete search history.

*Primary Examiner*—Kent L Bell
(74) *Attorney, Agent, or Firm*—James A. Lucas; Driggs, Hogg, Daugherty & Del Zoppo Co., LPA

(57) ABSTRACT

A hybrid male *asparagus* plant (*Asparagus officinalis*) denoted 'NJ953' has many desirable traits including vigorous plant growth, high yield, attractive spear morphology, good resistance to rust (*Puccinia asparagi*) and good field tolerance to *asparagus* root rot (*Fusarium oxysporum*) and *asparagus* crown rot (*Fusarium mondiforme*). These desirable traits have been shown to be transmissible to its progenies. The invention relates to plants and plant parts of 'NJ953' plant. The invention further relates to hybrid *asparagus* seeds and plants produced by crossing the *asparagus* 'NJ953' plant with another *asparagus* plant.

3 Drawing Sheets

Latin name of the genus and species: The Latin name is *Asparagus officinalis.*

Variety denomination: The varietal denomination is 'NJ953'.

BACKGROUND OF THE INVENTION

For an *asparagus* plant to be commercially viable and profitable, good yield is essential. It is well known that *asparagus* is susceptible to a number of diseases. Among the most devastating are rust caused by *Puccinia asparagi* d.c., (Kahn et al. 1952) and crown rot caused by *Fusarium oxysporum*, root rot caused by *Fusarium proliferatum* (syn=*Fusarium moniliforme*) (Johnston et al., 1979; Guerrero et al., 1999). Of course, the presence of these diseases adversely impacts the yields and therefore the profitability of the product. Accordingly, resistance to these diseases is important to commercial success.

BRIEF SUMMARY OF THE INVENTION

This invention herein described relates to a new and distinct *asparagus* plant, which was developed as an elite hybrid with many characteristics desired by growers and consumers. The performance of this hybrid was reproduced and evaluated at a cultivated area located near Bridgeton, N.J. This invention is distinguished particularly as to its desirable traits of vigorous growth habit, higher yield, attractive spear quality, good field resistance to rust (*Puccinia asparagi*) and good field tolerance to root and crown rot (*Fusarium oxysporum*) and (*Fusarium moniliforme*).

BRIEF SUMMARY OF THE DRAWINGS

The color notations have been selected from observations as compared with the Munsell Limit Color Cascade. Colors are approximate as color depends on density of growth, horticultural practices, such as light level, fertilization rate, print resolution and other conditions and, therefore, the color characteristics of this new variety should be determined with reference to the observations described herein, rather than from this illustration alone. Furthermore, the coloration is not considered to be a distinguishing feature of this new variety.

DETAILED DESCRIPTION OF THE INVENTION

Figure 1:
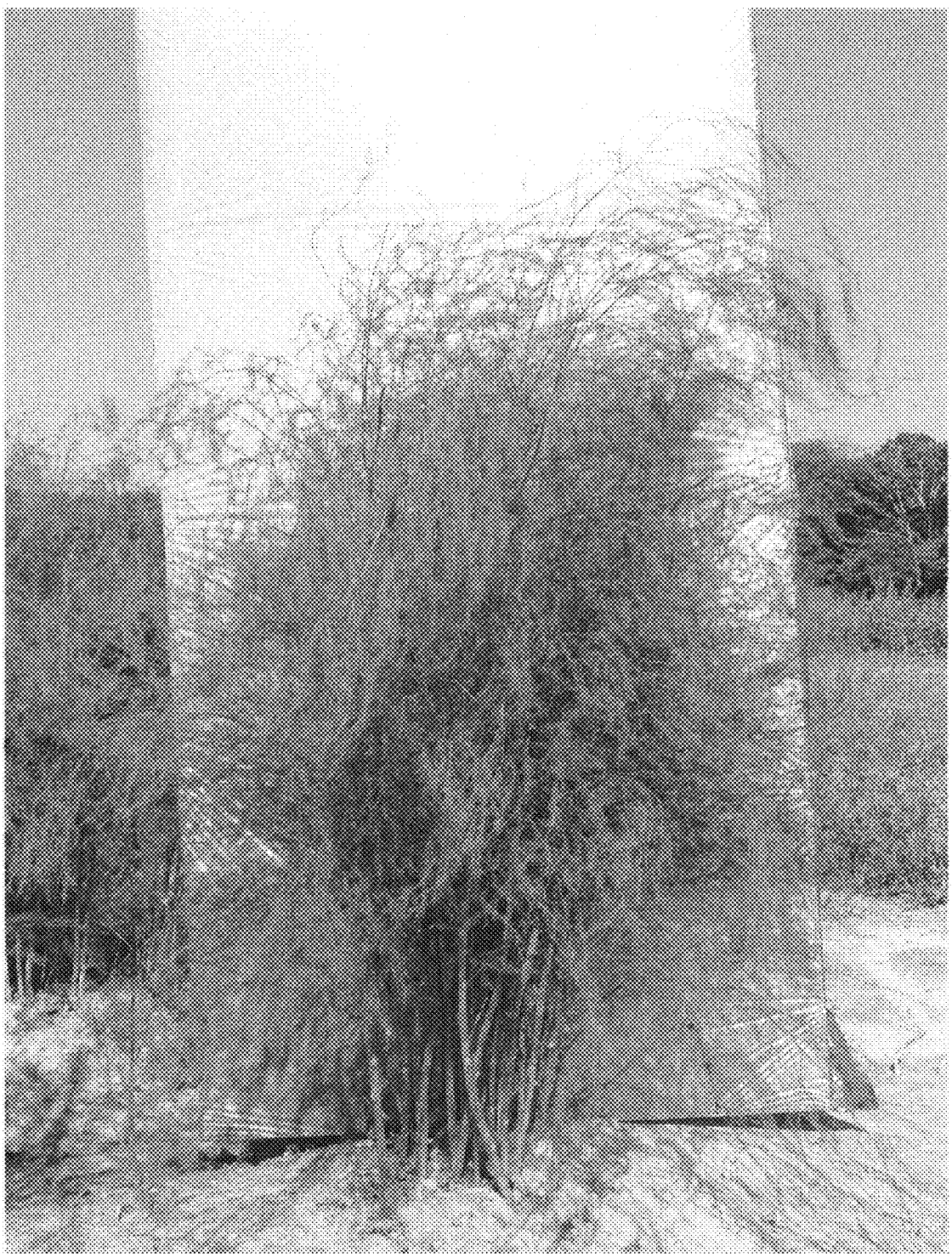
FIG. 1 shows in color a typical 'NJ953' plant of the new variety as it appears in a field under normal conditions.
Figure 2:
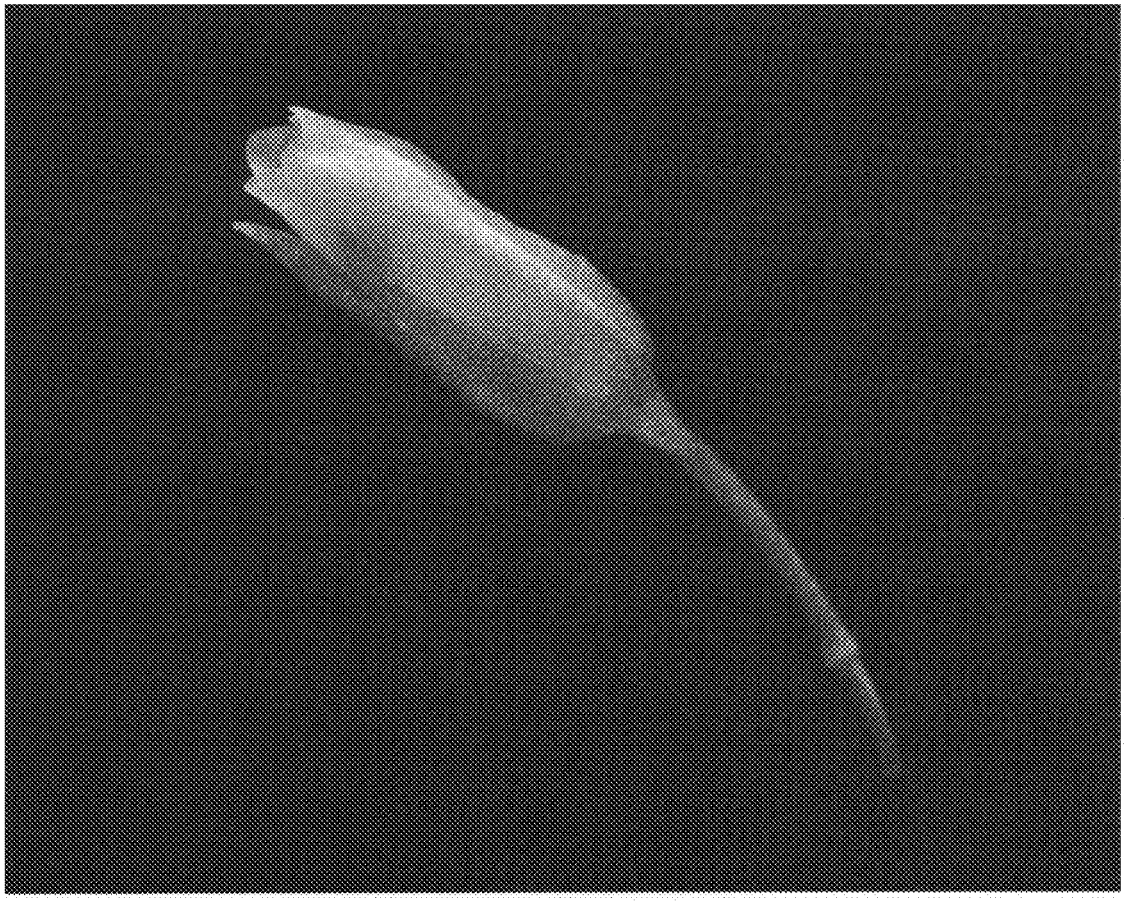
FIG. 2 shows in color a typical 'NJ953' flower as it appears in a field under normal conditions.
Figure 3:
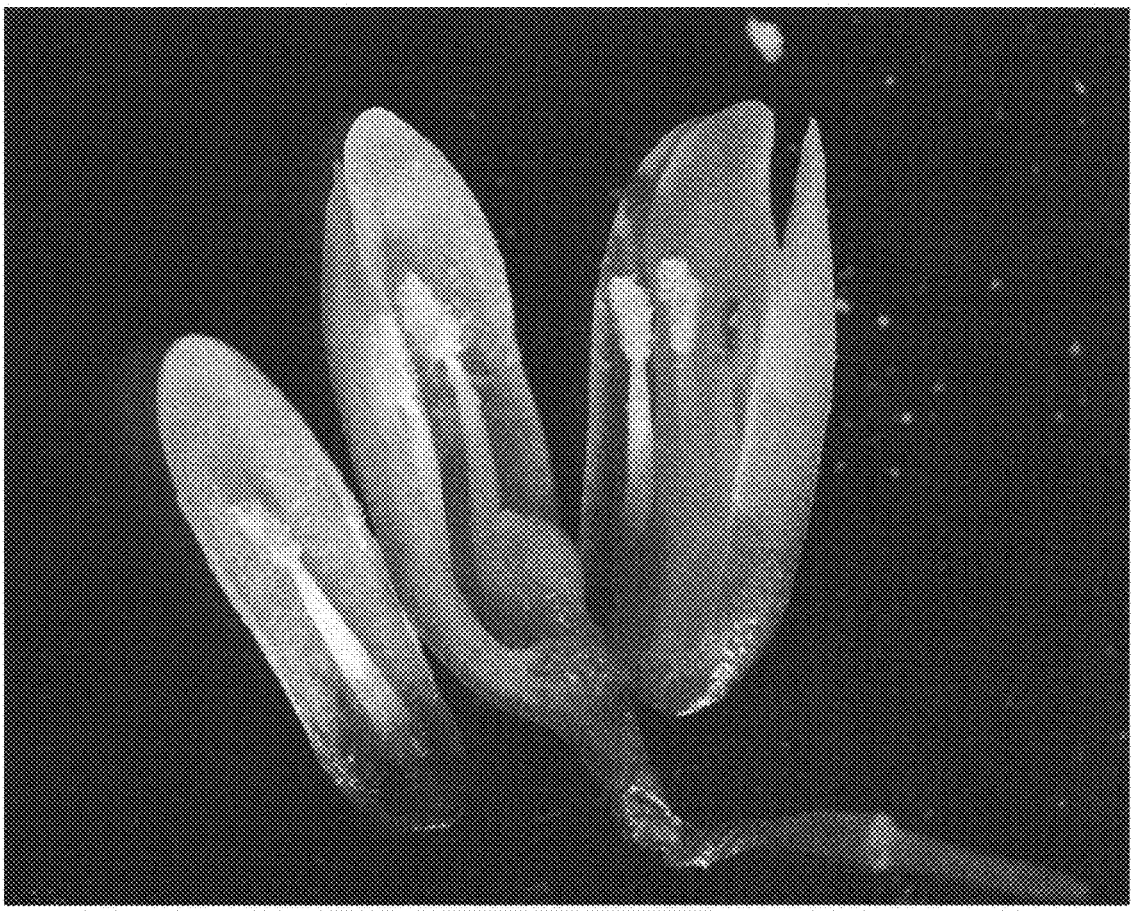
FIG. 3 shows in color a cut-open view of a typical 'NJ953' flower.

An extensive program of *asparagus* plant development, carried out in a cultivated area in the vicinity of Bridgeton, N.J., has resulted in the development of the *asparagus* hybrid 'NJ953' with many desirable traits.

*Asparagus* (*Asparagus officinalis* Linn.) is a dioecious species with individual plants being either male or female in sex. In addition to differences in morphology, 'cultivars' may also differ in local adaptation, yield, disease resistance, and longevity. Desirable cultivars are developed by crossing of elite male and female parents. Both male and female parents transmit traits such as disease resistance, yield, and spear morphology to their progenies. This invention relates to new and distinct *asparagus* hybrid designated as 'NJ953'. Disease resistance of the kind found in the 'NJ953' plant will allow growers to plant the hybrid in areas where rust, and *Fusarium* crown and root rot now prevent profitable culture of susceptible varieties.

*Asparagus* can be clonally propagated by crown division. Crown is the structure where shoots and roots join together. Division or separation at the crown area will allow the propagation of *asparagus*. When propagated by crown division, successive generations of 'NJ953' have similar morphological appearance and possess the same desirable characteristics as the original 'NJ953' plant.

*Asparagus* can also be clonally propagated by tissue culture. An *asparagus* shoot tip or meristem when cultured on appropriate nutrient medium and appropriate conditions can grow, develop, and regenerate into a plant. Also, *asparagus* plant parts such as a spear segment when cultured on appropriate nutrient medium and appropriate conditions can grow, develop, and regenerate into an *asparagus* plant. Such plant can be efficiently divided and multiplied in appropriate nutrient medium. A 'NJ953' plant propagated by such tissue culture has been found to retain the same desirable characteristics as the original 'NJ953' plant.

The 'NJ953' plant is a male plant. When crossed with different female plants, *asparagus* 'NJ953' can transmit many of its desirable traits including vigorous growth habit, higher yield, desirable spear morphology, good levels of resistance to rust (*Puccinia asparagi*), stem blight (*Phomopsis asparagi*) and field tolerance to root and crown rot (*Fusarium oxysporum*) and (*Fusarium moniliforme*) to its progenies.

Tables 1 and 2 show that in yield and disease resistance the progenies of 'NJ953' compare very favorably to Jersey Giant (U.S. Plant Pat. No. 6,624) and Jersey Knight (U.S. Plant Pat. No. 5,551) two of most popular *asparagus* varieties in the world today.

TABLE 1

| | Jersey Giant | Jersey Knight | 'NJ953' |
|---|---|---|---|
| Yield, LB/Acre | 5402 | 4435 | 6046 |
| Rust resistance* | 5.5 | 7 | 6.5 |
| *Fusarium* tolerance | Tolerant | Tolerant | Tolerant |

The data is based on a trial at an agriculture research center in Bridgeton, New Jersey. The trial was planted in 1998. The above data represents the average of the data collected from 2000 to 2005 from 2 to 7 year old plants.
Rust resistance*: 0: no resistance, 10: complete resistance.

TABLE 2

| | Jersey Giant 56 (female) × 22-8 (male) | Jersey Knight 277C (female) × 22-8 (male) | 56 (female) × 'NJ953' (male) |
|---|---|---|---|
| Yield, LB/Acre | 4940 | 4096 | 6044 |
| Rust resistance* | 5.3 | 6.4 | 6.2 |
| *Fusarium* tolerance | Tolerant | Tolerant | Tolerant |

Data from a trial at an agriculture research center in Bridgeton, New Jersey. The trial was planted in 2000. Average data from 2003 to 2006 from 3-6 year old plants.
Rust resistance*: 0: no resistance, 10: complete resistance.

BOTANICAL DESCRIPTION

Data that distinguishes *asparagus* plant 'NJ953' from other *asparagus* varieties that have been internally developed, as well as *asparagus* plants that are known and available commercially in the markets have been accumulated and are presented below.

The data (averages from 3 clones) is assembled in Table 3:

TABLE 3

| *ASPARAGUS* PLANT: 'NJ953' |
|---|
| Stalk data: |
| Number of nodes below first branch: 28.33.<br>Distance from crown to first branch: 59.48 cm.<br>Number of branches: 53.<br>Distance between first and last branch: 141.82 cm.<br>Internode length between branches: 2.7 cm.<br>Number of cladophyll nodes beyond last branch: 35.<br>Length beyond last branch: 22.33 cm.<br>Branch color: Color No. 21-13.<br>Largest stalk diameter: 21 mm.<br>Mean diameter of three largest stalks: 17.83 mm.<br>Length of longest head stalk: 223.63 cm.<br>Number of stalks: 30.<br>Mature stalks color, bloom removed: Color No. 21-13. |
| Flower data: |
| All vegetative and reproduction parts glabrous and appearing non-glandular.<br>Number of flowers per cluster: observed 1-4, typically 2.<br>Tepals: Observed: 6 in 2 whorls, forming campanulate corolla at anthesis, syntepalous for lowest 1 mm, free above, 4-6 mm long, 1.4-1.9 mm wide, dorsally slightly thickened,<br>apex outer surface margin color 25-2,<br>apex outer surface middle (vertical) color 24-9,<br>apex inner surface margin color 24-3,<br>apex inner surface middle (vertical) color 23-8,<br>base outer surface color 28-11,<br>base outer surface middle color 32-13,<br>base inner surface color 24-7,<br>base inner surface middle color 24-7,<br>Typical: straight in bud, recurved apically at anthesis, margin entire, strongly membranous; apex bluntly acute to obtuse, often twisted or crinkled after anthesis due to drying out of membranous area.<br>Flower width at midpoint: 2.4 mm.<br>Flower diameter: 2.4 mm. |
| Cladophyll data: |
| Average number per node: 5.2.<br>Shape: linear, filiform, needle-like; apex acute; base cunneate, margin-entire, color-21-11 throughout.<br>Length: 16.5 mm; width: 0.05 mm. |
| Leaf data: |
| Main stem leaves scale-like, triangular, leaves at 15 cm to 30 cm from soil level average 15 mm long, 14 mm wide at base, membranous: apex acuminate; base truncate; margin hyaline; Color-27-11 abaxial; 28-10 adaxial.<br>Terminal branch leaves scale-like, triangular, average 3.5 mm long, 2 mm wide at base, membranous; apex acuminate; base truncate; margin erose, hyaline. Color: 26-8 abaxial; 25-8 adaxial.<br>Typical: subtending inflorescence branches triangular, scale-like, membranous, especially towards margins, not keeled or winged, with small hanging appendix from dorsal midvein close to stem; margins entire; apex acute. |
| Reproductive Organs |
| Stamens - 6 in number, each stamen fused to middle of inner side of a tepal, free from tepals and each other, arranged in tepal sinuses and in dorsal position to innermost whorl of tepals; length: 3-4.5 mm.<br>Filaments-filiform, slightly widened towards base, 3-3.5 mm long, 0.15-0.2 mm wide at top, about 0.5-0.55 mm wide at base.<br>Anthers elliptic, 0.7-0.9 mm long and about 0.5 mm wide at base, longitudinally dehiscent, introrse to slightly latorose, base sagittate, apex obtuse, with small acuminate tip.<br>Rudimentary Gynoecium, rudimentary, - tricarpellate, with noticeable sutures along ovary.<br>Rudimentary Ovary sessile, elliptic to obovate, 1.2-1.8 mm long, 0.9-1.3 mm wide at anthesis, color 21-10; style 1, rudimentary, 0.05 mm long, color 24-5; Stigma absent. |

What is claimed is:

1. A new and distinct hybrid variety of a male *asparagus* plant 'NJ953' as herein shown and described.

* * * * *